(12) United States Patent
Deissler et al.

(10) Patent No.: US 6,387,974 B1
(45) Date of Patent: May 14, 2002

(54) POLYMERIC ADSORBENTS AND METHOD OF PREPARATION

(75) Inventors: Karl Chaplin Deissler, Warminster; Marlin Kenneth Kinzey, Philadelphia; John Joseph Maikner, Quakertown; Robert E. Rosen, Melrose Park, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/923,935

(22) Filed: Aug. 7, 2001

Related U.S. Application Data

(60) Provisional application No. 60/224,373, filed on Aug. 11, 2000.

(51) Int. Cl.[7] ................................................. C08F 36/00
(52) U.S. Cl. ...................... 521/150; 210/645; 210/656; 424/486; 521/146; 521/149; 530/815
(58) Field of Search ........................... 424/486; 210/656, 210/645; 521/64, 146, 150; 530/815

(56) References Cited

U.S. PATENT DOCUMENTS 4,686,269 A    8/1987    Tokunaga et al.

FOREIGN PATENT DOCUMENTS

| JP | 57-98504   | 6/1982 |
|----|------------|--------|
| JP | 61-141704  | 6/1986 |

OTHER PUBLICATIONS

Lloyd, L.L. and Warner, F.P., Preparative High Performance Liquid Chromatography on a Unique High–Speed Macroporous Resin, *J. Chromatography*, vol. 512, pp 365–376 (1990).

Lloyd, L.L., Rigid Macroporous Copolymers as Stationary Phases in High Performance Liquid Chromatography, Review, *J. Chromatography*, vol. 544, pp 201–217 (1991).

*Primary Examiner*—Morton Foelak
(74) *Attorney, Agent, or Firm*—Thomas J. Howell

(57) ABSTRACT

Macroporous polymers having selected porosity and permeability characteristics that provide rigid polymer matrices suitable for use in medium and high pressure reversed phase liquid chromatography (RPC) are disclosed. A method for preparing the polymers using selected mixed porogens in selected proportions relative to the monomer phase is also disclosed. The polymers are especially useful as stationary phases in large scale chromatography columns without developing increased pressures during prolonged use, while maintaining good chromatographic performance for targeted biomolecules, such as insulin.

19 Claims, No Drawings

POLYMERIC ADSORBENTS AND METHOD OF PREPARATION

CROSS REFERENCE TO RELATED PATENT APPLICATIONS

This is a non-provisional application of prior pending U.S. provisional application serial No. 60/224,373 filed Aug. 11, 2000.

BACKGROUND

This invention relates to novel macroporous polymers having selected porosity and permeability characteristics that provide rigid polymer matrices suitable for use in medium and high pressure reversed phase liquid chromatography (RPC). The polymers are especially useful as stationary phases in large scale chromatography columns without developing increased pressures during prolonged use.

Stationary phases useful in RPC, especially in high performance preparative mode (such as required in the separation and purification of biomolecules), must be mechanically rigid to withstand the high operating pressures generated within the chromatography columns. Silica matrices, which have been commonly used for these applications in the past, have satisfactory mechanical rigidity; however, silica matrices cannot be operated under high pH conditions, which severely limits their use in a wide range of biomolecule separations. This factor limits the purification options available to the process chromatographer, and adversely affects the production lifetime of silica media (they degrade faster because they cannot be cleaned under aggressive conditions), resulting in poorer overall economics of commercial manufacturing processes.

Stationary phases based on organic polymers, on the other hand, call typically be operated over a very wide range of pH conditions, providing greater utility in biomolecule separations. The chromatographer has the option to develop a high pH process, which may offer such benefits as improved solubility, selectivity and capacity characteristics of the separation media for certain molecules. In addition, polymeric resins may be cleaned aggressively, under high pH conditions, thus improving the column lifetime and, consequently, process economics. However, current polymeric stationary phases are somewhat compressible at the medium to high pressure conditions used in high-performance biomolecule separations. This compressibility is detrimental to separation processes because it limits the range of operable flowrates, and it can degrade the integrity of the polymer bed in the column. For example, the following references disclose polymers used at column conditions representative of high-pressure analytical operations (less than 0.5 cm internal diameter columns), where "wall effects" are known to minimize polymer compressibility; however, these references do not disclose operations in larger scale, high-pressure commercial chromatography columns where one would expect additional pressure buildup from polymer compressibility due to the absence of wall effects: Lloyd, L. L. and Warner, F. P., *Preparative High Performance Liquid Chromatography on a Unique High-Speed Macroporous Resiv, J. Chromatography,* Vol. 512, pp 365–376 (1990); and Lloyd, L. L., *Rigid Macroporous Copolymers as Stationary Phases in High Performance Liquid Chromatography, Review, J. Chromatography,* Vol. 544, pp 201–217 (1991).

Conventional macroporous copolymers produced from the suspension polymerization of divinylbenzene (DVB)-containing monomer mixtures in the a presence of a non-solvent represent polymers having a wide range of pore size distributions and surface areas. For example, U.S. Pat. No. 4,686,269 discloses a method to prepare polymers for use in analytical scale liquid chromatography columns (internal diameter of 0.8 centimeter) having average particle diameters from 0.5 to 50 microns and containing at least 60% polyvinylaromatic monomer, by polymerizing the monomers with 50 to 300% of organic cosolvents, based on total weight of monomer; the reference does not disclose a method to prepare polymers having selected porosity and permeability characteristics that provide rigid polymer matrices that do not compress under the high pressure use conditions common in production scale chromatography columns, that is, those having internal diameters of 2 to 100 centimeters, typically from 5 to 80 centimeters.

Polymer compressibility translates to restricted flow through the separation media, producing additional back-pressure in the chromatography system, and ultimately, longer cycle times. There is a need for a polymeric stationary phase that can withstand, without significant compression, the medium to high operating pressures generated under typical RPC process conditions. In addition, it is essential that the stationary phase also have satisfactory mass transfer and capacity characteristics for certain targeted classes of biomolecules in order to yield the desired chromatographic performance.

The problem addressed by the present invention is to provide a macroporous polymer stationary phase suitable for biomolecule separation and purification, while at the same time providing satisfactory pressure and flow characteristics during RPC.

SUMMARY OF INVENTION

The present invention provides a macroporous polymer comprising polymerized monomer units of (a) 50 to 100 percent by weight of one or more polyvinylaromatic monomer, and (b) zero to 50 percent by weight of one or more monounsaturated vinylaromatic monomer; wherein the polymer has (i) a total porosity of 0.7 to 2 cubic centimeter per gram; (ii) an operational mesoporosity of 0.7 to 1.9 cubic centimeter per gram; (iii) an average particle size diameter of 2 to 600 microns; (iv) a surface area of 200 to 1500 square meters per gram; (v) a flow resistance value from 700 to less than 1,800 at 10 bar pressure and from 1,500 to less than 7,000 at 60 bar pressure; and (vi) a total insulin capacity of 75 to 150 grams insulin/liter of polymer and a dynamic insulin capacity of 60 to 150 grams insulin/liter of polymer.

In a preferred embodiment, the present invention provides the aforementioned macroporous polymer having (a) a surface area of 400 to 1000 square meters per gram; (b) an operational mesoporosity of 0.9 to 1.4 cubic centimeter per gram; (c) an average particle size diameter of 10 to 75 microns; (d) a flow resistance value from 700 to less than 1,500 at 10 bar pressure and from 1,500 to less than 5,000 at 60 bar pressure; and (e) a total insulin capacity of 90 to 150 grams insulin/liter of polymer and a dynamic insulin capacity of 75 to 150 grams insulin/liter of polymer.

The present invention also provides a process for preparing a macroporous polymer comprising polymerizing zero to 50 percent monovinylaromatic monomer and 50 to 100 percent polyvinylaromatic monomer, in the presence of 100 to 170 percent of a porogen mixture comprising a hydrophobic porogen and a hydrophilic porogen, and 0.5 to 10 percent free radical polymerization initiator, in an aqueous suspension; wherein all percent amounts are based on total weight of monomer; and wherein: (a) the hydrophilic porogen is present in a weight ratio of greater than 1.2/1 up to 3/1 relative to the hydrophobic porogen; and (b) the hydrophilic porogen is selected from one or more ($C_4$–$C_{10}$)alkanol and the hydrophobic porogen is selected from one or more ($C_7$–$C_{10}$)aromatic hydrocarbon and ($C_6$–$C_{12}$)saturated hydrocarbon.

The present invention further provides a method for purifying aqueous solutions of mixed biomolecules, comprising contacting the aqueous solution with the aforementioned macroporous polymer in a liquid chromatography column having an internal diameter of 2 to 100 centimeters, wherein the column is operated at a pressure of 10 to 100 bar.

DETAILED DESCRIPTION

We have discovered that novel macroporous polymers useful for large scale separation and purification of biomolecules by high pressure liquid reverse phase chromatography can be prepared having selected porosity and permeability characteristics. In particular, we have discovered that using specific porogen solvents in specific proportions relative to the monomer phase under specific polymerization conditions unexpectedly provides the rigid polymer matrices of the present invention. The novel macroporous polymers may be used in high pressure RPC without significant compressibility and pressure buildup while maintaining good throughput and capacities (dynamic and equilibrium) for targeted biomolecules.

As used throughout the specification, the following terms shall have the following meanings, unless the context clearly indicates otherwise.

The term "alkyl (meth)acrylate" refers to either the corresponding acrylate or methacrylate ester; similarly, the term "(meth)acrylic" refers to either acrylic or methacrylic acid and the corresponding derivatives, such as esters or amides. All percentages referred to will be expressed in weight percent (%), based on total weight of polymer or composition involved, unless specified otherwise. The term "copolymer" refers to polymer compositions containing units of two or more different monomers, including positional isomers. The following abbreviations are used herein: g=grams; ppm=parts per million by weight/volume, cm=centimeter, mm=millimeter, ml=milliliter, L=liter. Unless otherwise specified, ranges listed are to be read as inclusive and combinable and temperatures are in degrees centigrade (°C.).

The macroporous polymers useful as RPC stationary phases have increased structural rigidity compared to existing materials, making the polymers suitable for use in commercial-scale manufacturing processes. Increased structural rigidity has been achieved by modification of the structure of polymer matrix by using selected polymerization conditions.

Modifying the polymer matrix porosity is important in preparing the macroporous polymers of the present invention. To be effective in separating large biomolecules, a stationary phase preferably has an open, porous structure that enables rapid diffusion of molecules into and out of the matrix. In addition, a high level of porosity affords a large surface area, which in turn providing a high capacity of the matrix for the target molecule. Most modern, commercial polymeric RPC stationary phases appear to be designed around these criteria, and are used under lower pressure conditions (typically, from 1 bar up to less than 10 bar and preferably from 1 to 5 bar; 1 bar pressure=$10^5$ Pascal or $10^5$ Pa). However, at higher pressure conditions (typically from 10 bar to 100 bar) these matrices are compressible. The macroporous polymers of the present invention have increased polymer rigidity, and at the same time have preserved high capacity and rapid intraparticle diffusion for target molecules.

The macroporous polymers of the present invention are useful for purifying biomolecule mixtures dissolved in aqueous solutions by contacting the solution with the macroporous polymer in a liquid chromatography column having internal diameters of 2 to 100, preferably from 5 to 80 and more preferably from 10 to 50 centimeters, where the column is operated at a pressure of 10 to 100 and preferably from 20 to 80 bar. Typically, preparative scale RPC is performed in 10 to 50 centimeter chromatography columns at 20 to 80 bar pressures.

Selected polymerization conditions represent an important factor in preparing macroporous polymers of the present invention. Selected ratios of mixed porogen relative to the monomer phase, as well as the ratio of hydrophilic porogen relative to hydophobic porogen, are the key parameters believed to provide the macroporous polymers of the present invention.

While not wishing to be bound by theory, we believe that, in the case of the present invention, the polymer matrix density is altered to allow more solid polymer per unit volume of total polymer, thereby increasing matrix rigidity, with a consequently increased capacity for target molecules. The particular selection of the amount of porogen relative to monomer and the balance of hydrophobic versus hydrophilic porogen types is believed to affect the pore size distribution in a manner favorable to binding of target molecules (in this case, biomolecules) while at the same time providing improved matrix rigidity.

Crosslinked macroporous copolymers of the present invention are typically spherical copolymer beads having average particle size diameters from 2 to 600 microns ($\mu$m). Polymers useful for the separation and purification of biomolecules via high performance reverse phase liquid chromatography (such as in columns from 2 to 100 cm in diameter) typically have average particle size diameters from 2 to 150, preferably from 5 to 100, more preferably from 10 to 75 and most preferably from 10 to 30 $\mu$m. Polymers useful for the separation and isolation of biomolecules via large scale adsorption processes (such as in columns up to several meters in diameter or in fermentation broths) typically have average particle size diameters from greater than 150 up to 600, preferably from 200 to 500 and more preferably from 250 to 400 $\mu$m.

The macroporous polymers of the present invention are typically produced by suspension polymerization, and possess surface areas from 200 to 1500, preferably from 300 to 1200 and more preferably from 400 to 1000 square meters per gram ($m^2$/g). The macroporous polymers are preferably those of the type described in U.S. Pat. No. 4,382,124, for example, in which porosity is introduced into the copolymer beads by suspension-polymerization in the presence of a porogen (also known as "phase extender" or "precipitant"), that is, a solvent for the monomer but a non-solvent for the polymer. Conventional macroporous polymers, such as those prepared according to U.S. Pat. No. 4,382,124, typically encompass the use of a wide range of porogen types, porogen concentrations relative to the monomer phase, monomer types, crosslinking monomer types, crosslinker levels, polymerization initiators and initiator concentrations. The present invention, however, is based on the discovery that macroporous polymers prepared using certain selected porogen types, used in specific concentrations relative to the monomer phase, with specific monomers and selected levels of crosslinking, together with selected polymerization initiator concentrations, have unexpectedly rigid polymer structures corresponding to improved performance in the separation and purification of biomolecules via high performance reverse phase liquid chromatography.

Suitable polyvinylaromatic monomers that may be used in the preparation of the macroporous polymers useful in the present invention include, for example, one or more monomer selected from divinylbenzene, trivinylbenzene, divinyltoluene, divinylnaphthalene, divinylanthracene and divinylxylene; it is understood that any of the various positional isomers of each of the aforementioned crosslinkers is suitable; preferably the polyvinylaromatic monomer is divinylbenzene. Typically the macroporous polymer comprises 50 to 100%, preferably 65 to 100% and more preferably 75 to 100% polyvinylaromatic monomer units.

Optionally, aliphatic crosslinking monomers, such as ethyleneglycol diacrylate, ethyleneglycol dimethacrylate, trimethylolpropane triacrylate, trimethylolpropane trimethacrylate, glycidyl methacrylate, diethyleneglycol divinyl ether and trivinylcyclohexane, may also be used in addition to the polyvinylaromatic crosslinker. When used, the aliphatic crosslinking monomers typically comprise as polymerized units, from zero to 20%, preferably from zero to 10%, and more preferably from zero to 5% of the macroporous polymer, based on the total monomer weight used to form the macroporous copolymer.

Suitable monounsaturated vinylaromatic monomers that may be used in the preparation of the macroporous copolymers useful in the present invention include, for example, styrene, α-methylstyrene, $(C_1-C_4)$alkyl-substituted styrenes, halo-substituted styrenes (such as dibromostyrene and tribromostyrene), vinylnaphthalene and vinylanthracene; preferably the monounsaturated vinylaromatic monomer is selected from one or more of styrene and $(C_1-C_4)$alkyl-substituted styrenes. Included among the suitable $(C_1-C_4)$alkyl-substituted styrenes are, for example, ethylvinylbenzenes, vinyltoluenes, diethylstyrenes, ethylmethylstyrenes and dimethylstyrenes; it is understood that any of the various positional isomers of each of the aforementioned vinylaromatic monomers is suitable; preferably the monounsaturated vinylaromatic monomer is ethylvinylbenzene. Typically, the macroporous polymer comprises zero to 50%, preferably zero to 35% and more preferably zero to 25%, monounsaturated vinylaromatic monomer units.

Optionally, non-aromatic vinyl monomers, such as aliphatic unsaturated monomers, for example, vinyl chloride, acrylonitrile, (meth)acrylic acids and alkyl esters of (meth)acrylic acids (alkyl (meth)acrylates) may also be used in addition to the vinylaromatic monomer. When used, the non-aromatic vinyl monomers typically comprise as polymerized units, from zero to 20%, preferably from zero to 10%, and more preferably from zero to 5% of the macroporous copolymer, based on the total monomer weight used to form the macroporous copolymer.

Preferred macroporous polymers are selected from one or more of divinylbenzene copolymer, styrene-divinylbenzene copolymer, divinylbenzene-ethylvinylbenzene copolymer and styrene-ethylvinylbenzene-divinylbenzene copolymer; more preferable are divinylbenzene-ethylvinylbenzene and styrene-ethylvinylbenzene-divinylbenzene polymers.

Porogens useful for preparing the macroporous polymers of the present invention include hydrophobic porogens, such as $(C_7-C_{10})$aromatic hydrocarbons and $(C_6-C_{12})$saturated hydrocarbons; and hydrophilic porogens, such as $(C_4-C_{10})$alkanols and polyalkylene glycols. Suitable $(C_7-C_{10})$ aromatic hydro-carbons include, for example, one or more of toluene, ethylbenzene, ortho-xylene, meta-xylene and para-xylene; it is understood that any of the various positional isomers of each of the aforementioned hydrocarbons is suitable. Preferably the aromatic hydrocarbon is toluene or xylene or a mixture of xylenes or a mixture of toluene and xylene. Suitable $(C_6-C_{12})$saturated hydrocarbons include, for example, one or more of hexane, heptane and isooctane; preferably, the saturated hydrocarbon is isooctane. Suitable $(C_4-C_{10})$alkanols include, for example, one or more of isobutyl alcohol, tert-amyl alcohol, n-amyl alcohol, isoamyl alcohol, methyl isobutyl carbinol (4-methyl-2-pentanol), hexanols and octanols; preferably, the alkanol is selected from one or more $(C_5-C_8)$alkanols, such as, methyl isobutyl carbinol and octanol. Preferably, the porogen mixture comprises a hydrophilic porogen selected from one or more $(C_5-C_8)$alkanol and a hydrophobic porogen selected from one or more $(C_7-C_{10})$aromatic hydrocarbon.

Typically, the total amount of porogen used to prepare the polymers of the present invention is from 100 to 170%, preferably from 110 to 160%, more preferably from 115 to 150% and most preferably from 120 to 140%, based on weight of the monomers. At porogen levels above 170%, the polymers have poor flow resistance values (high compressibility) at high pressure conditions in packed columns; at porogen levels below 100%, the polymers have poor chromatographic properties (as measured by insulin capacity in column flow-through tests). In addition, the porogens used to prepare the polymers of the present invention are based on a mixed solvent system, comprising a hydrophobic solvent ("hydrophobic" porogen) and a less hydrophobic solvent ("hydrophilic" porogen). It is understood that the hydrophilic porogen has some limited water solubility (for example, 0.5 to 5%) and is more water soluble than the hydrophobic porogen (typical water solubility of 10 to 100 ppm, or less).

Typically, the ratio of hydrophilic porogen to hydrophobic porogen is from greater than 1.2/1 up to 3/1, preferably from 1.3/1 to 2.7/1, more preferably from 1.4/1 to 2.5/1 and most preferably from 1.6/1 to 2.4/1. At hydrophilic/hydrophobic porogen ratios of about 1.2/1 and lower, the polymers having acceptable flow resistance performance also have decreased chromatographic performance (measured by restricted mass transfer access in the insulin capacity test). At hydrophilic/hydrophobic porogen ratios above 3/1, the polymers would have decreased overall capacity performance (measured by decreased amounts of insulin sorbed during the column flow test). Typically, the mixed porogens comprise a $(C_7-C_{10})$ aromatic hydrocarbon and a $(C_4-C_{10})$alkanol; preferably, the mixed porogens comprise xylenes and methyl isobutyl carbinol.

Polymerization initiators useful in preparing polymers of the present invention include monomer-soluble initiators such as peroxides, hydroperoxides and related initiators; for example benzoyl peroxide, tert-butyl hydroperoxide, cumene peroxide, tetralin peroxide, acetyl peroxide, caproyl peroxide, tert-butyl peroctoate (also known as tert-butylperoxy-2-ethylhexanoate), tert-amyl peroctoate, tert-butyl perbenzoate, tert-butyl diperphthalate, dicyclohexyl peroxydicarbonate, di(4-tert-butylcyclohexyl) peroxydicarbonate and methyl ethyl ketone peroxide. Also useful are azo initiators such as azodiisobutyronitrile, azodiisobutyramide, 2,2'-azo-bis(2,4-dimethylvaleronitrile), azo-bis(α-methyl-butyronitrile) and dimethyl-, diethyl- or dibutyl azo-bis(methylvalerate). Preferred peroxide initiators are diacyl peroxides, such as benzoyl peroxide, and peroxyesters, such as tert-butyl peroctoate and tert-butyl perbenzoate; more preferably, the initiator is benzoyl peroxide. Suitable use levels of peroxide initiator are 0.5% to 10%, preferably from 1 to 9%, more preferably from 2 to 7% and most preferably from 3 to 5%, based on the total weight of vinyl monomers. Most preferably, the free radical initiator is present at 2 to 7 percent, based on total weight of monomer, and is selected from one or more diacyl peroxide and peroxyester.

Dispersants and suspending agents useful for preparing the macroporous polymers of the present invention are nonionic surfactants having a hydroxyalkylcellulose backbone, a hydrophobic alkyl side chain containing from 1 to 24 carbon atoms, and an average of from 1 to 8, preferably from 1 to 5, ethylene oxide groups substituting each repeating unit of the hydroxyalkyl-cellulose backbone, the alkyl side chains being present at a level of 0.1 to 10 alkyl groups per 100 repeating units in the hydroxyalkylcellulose backbone. The alkyl group in the hydroxyalkylcellulose may contain from 1 to 24 carbons, and may be linear, branched or cyclic. More preferred is a hydroxyethylcellulose containing from 0.1 to 10 ($C_{16}$)alkyl side chains per 100 anhydroglucose units and from about 2.5 to 4 ethylene oxide groups substituting each anhydroglucose unit. Typical use levels of dispersants are from about 0.01 to about 4%, based upon the total aqueous-phase weight.

Other dispersants and suspending agents useful for making the macroporous polymers of the present invention are polymers containing hydrophilic backbones, which can orient their lipophilic portions to the monomer phase and their hydrophilic portions to the aqueous phase at the interface of the two phases. These polymeric dispersants include celluloses, polyvinyl pyrrolidones, polyvinyl alcohols, starches and the like. Mixtures of dispersants may also be used. These other dispersants tend to be less preferred, as they tend to produce a somewhat greater amount of agglomerated or otherwise undesirable material.

A typical macroporous copolymer preparation, for example, may include preparation of a continuous aqueous phase solution containing suspension aids (such as dispersants, protective colloids and buffers) followed by mixing with a monomer mixture containing 50 to 100% polyvinylaromatic monomer, free-radical initiator and 1 to 1.7 parts mixed porogen (hydrophobic and hydrophilic porogen) per one part monomer mixture. The monomer/mixed porogen combination is then polymerized at elevated temperature (typically at 40 to 120° C., preferably 60 to 100° C.; for 1 to 20 hours, preferably 3 to 15 hours, for example) and the porogens are subsequently removed from the resulting polymer beads by various means; for example, toluene, xylene and ($C_4$–$C_{10}$)alcohols may be removed by distillation or solvent washing, and polyalkylene glycols by water washing. The resulting macroporous copolymer is then isolated by conventional means, such as dewatering followed by drying.

Optionally, the preparation of the macroporous polymers may include an enzyme treatment to cleanse the polymer surface of residues of dispersants and suspending agents used during the polymerization. The enzyme treatment typically involves contacting the macroporous polymer with the enzymatic material (selected from one or more of cellulose-decomposing enzyme and proteolytic enzyme) during polymerization, following polymerization or after isolation of the polymer. Japanese Patent Applications No. 61-141704 and No. 57-98504 may be consulted for further general and specific details on the use of enzymes during the preparation of polymer resins. Suitable enzymes include, for example, cellulose-decomposing enzymes, such as β-1,4-glucan-4-glucano-hydrase, β-1,4-glucan-4-glucanhydrolase, β-1,4-glucan-4-glucohydrase and β-1,4-glucan-4-cellobiohydrase, for cellulose-based dispersant systems; and proteolytic enzymes, such as urokinase, elastase and enterokinase, for gelatin-based dispersant systems. Typically, the amount of enzyme used relative to the polymer is from 2 to 35%, preferably from 5 to 25% and more preferably from 10 to 20%, based on total weight of polymer.

The macroporous polymers of the present invention are especially useful in packed chromatography column applications where porosity and mechanical strength of the polymer allows for high performance separation and purification of biomolecules at high throughput rates without pressure buildup on prolonged use.

Optionally, the macroporous polymers may be coated or post-functionalized with various conventional ionizable functional groups (weak-acid functional group, such as a carboxylic acid group; weak-base functional group, such as a primary, secondary or tertiary amine functional group; strong acid functional group, such as sulfonic acid group; strong base functional group, such as quaternary ammonium chloride or hydroxide group) by known methods, such as conventional sulfonation, chloromethylation and amination.

The macroporous polymers of the present invention are characterized by improved permeability (low flow resistance) that is the result of the enhanced rigid polymer structure and the selected porosity introduced into the polymer during polymerization. The permeability (K) is related to the backpressure generated in a column through Darcy's Law (Equation 1):

$$\Delta P = \mu V / K(d_p)^2] \qquad \text{Equation 1}$$

where:

$\mu$ = viscosity (milliPascal·second or centipoise)

$V$ = linear velocity (cm/hr)

$\Delta P$ = pressure drop (bars)

$d_p$ = mean particle size of the polymer (microns)

The units of the above variables are expressed in their common form; it is understood that unit conversion is required to render Equation 1 dimensionless. The more rigid (that is, less compressible) the polymer, the greater the permeability of the polymer, translating to lower backpressure for any given combination of solvent viscosity, linear velocity and particle size. Under laminar flow conditions, which are typical for chromatographic separation and purification applications, the backpressure in a column can also be expressed by the Carman-Kozeny Equation (Equation 2):

$$\Delta P = 150 \cdot [(1-\epsilon)^2/\epsilon^3] \mu V/(d_p)^2 \qquad \text{Equation 2}$$

where:

$\epsilon$ = interparticle void volume ($cm^3$/$cm^3$)

References, such as *Fundamentals of Preparative and Nonlinear Chromatography*, G. Guiochon, S. Goshan Shirazi and A. Katti; Academic Press (1994) and *Unit Operations in Chemical Engineering*, W. L. McCabe, J. C. Smith and P. Harriott; McGraw Hill (1985), may be consulted for further general and specific details on Darcy's Law and the Carman-Kozeny Equation (Equations 1 and 2).

By combining Equations 1 and 2, it can be seen that permeability (or flow resistance) in the chromatography column is related to the interparticle void volume of the polymer resin bed (that is, the volume between polymer particles); $\epsilon$ is expressed as volume of voids per unit volume of polymer bed. This relationship is expressed by Equation 3:

$$1/K = 150 \cdot [(1-\epsilon)^2/\epsilon^3] \qquad \text{Equation 3}$$

For the purposes of the present invention, we define the characteristic "flow resistance" value of a polymer to be the inverse of the permeability. The characteristice "flow resistance" value is an indication of how well the polymer will perform under medium to high pressure conditions: low flow resistance values represent low compressibility and high flow resistance values represent poor compressibility.

Additionally, according to Darcy's Law, expressions for either the permeability or the flow resistance commonly include the particle size effect ($d_p$ in Equation 1). One objective of the present invention is to provide improved flow resistance via increased polymer rigidity, independent of particle size effects. It is understood that reduced particle size alone would, for a given polymer, generate higher backpressures as given by Equations 1 and 2.

Typically, macroporous polymers of the present invention have flow resistance values (that is, 1/K) from 700 to less than 1,800, preferably from 700 to less than 1,500 and more preferably less than 1,300 at operating pressures of 10 bar (medium pressure). At high pressure operation (represented by 60 bar), the macroporous polymers have flow resistance values from 1,500 to less than 7,000, preferably from 1,500 to less than 5,000 and more preferably less than 4,500. Macroporous polymers suitable for use in RPC have flow resistance values of (i) less than 1,800 at a pressure of 10 bar pressure and (ii) less than 7,000 at 60 bar pressure. Polymers having flow resistance values greater than the limits indicated above do not provide sufficient resistance to compression at the medium to high pressures found in commercial RPC columns and consequently suffer from reduced throughput and column pressure buildup during operation.

The macroporous polymers of the present invention are characterized by selected porosities and pore size distributions produced by the porogen types and ratios used to prepare the polymers. Porosities were determined using a Micromeretics™ ASAP-2400 nitrogen Porosimeter. Porosities according to IUPAC nomenclature are as follows:

| | | |
|---|---|---|
| Microporosity | = | pores less than 20 Ångstrom units |
| Mesoporosity | = | pores between 20 and 500 Ångstrom units |
| Macroporosity | = | pores greater than 500 Ångstrom units |

For the purposes of the present invention, "operational" microporosity is defined as pores having a diameter of less than 50 Ångstrom units and "operational" mesoporosity is defined as pores having diameters between 50 and 500 Ångstrom units. The slight difference between "operational" porosity, as used herein, and porosity defined according to IUPAC nomenclature is due to the fact that 50 Ångstrom units is a more suitable and appropriate cutoff point (compared to 20 Ångstrom units) in order to accommodate the sorption of biomolecules of interest in the macroporous polymers of the present invention.

The macroporous polymers of the present invention typically have a total porosity of 0.7 to 2, preferably from 0.9 to 1.8 and more preferably from 1.0 to 1.7 cm³/g. Typically, the macroporous polymers have an operational mesoporosity of 0.7 to 1.9, preferably from 0.8 to 1.7 and more preferably 0.9 to 1.4 cm³/g. Typically, the macroporous polymers have an operational microporosity from zero to 0.5, preferably from zero to 0.3, more preferably from zero to 0.2 and most preferably from zero to less than 0.1 cm³/g. Typically, the macroporous polymers have a macroporosity from zero to 0.6, preferably from zero to 0.5 and more preferably from zero to 0.3 cm³/g. Macroporosity values above about 0.6 cm³/g decrease the working capacity of the polymer for biomolecules of the targeted molecular size and shape, in terms of total capacity.

Insulin capacity is used as an indicator of the capability of a polymer matrix as a suitable medium for large scale separation and purification of biomolecules of similar size and molecular configuration. The macroporous polymers of the present invention typically have a dynamic insulin capacity of 60 to 150 g/L, preferably from 70 to 150 g/L and more preferably from 75 to 150 g/L. Typically, the macroporous polymers have a total insulin capacity of 75 to 150 g/L, preferably from 80 to 150 g/L and more preferably from 90 to 150 g/L. Dynamic capacity is a measure of how quickly the polymer matrix is able to take up the biomolecule and is defined as the insulin capacity at the breakthrough point where 1% leakage (relative to total insulin sorbed on the polymer) occurs. Insulin capacity is defined in g/L, that is, grams insulin/liter of polymer resin. Macroporous polymers of the present invention suitable for use in high performance, large scale preparative chromatography of biomolecules, typically have a combination of dynamic and total insulin capacity values of 60 and 75 g/L, respectively; preferably, 70 and 80 g/L, respectively; and more preferably 75 and 90 g/L, respectively.

The total capacity of the polymer resin for a given biomolecule (for example, insulin) is significant because it is related to the mass of the particular molecule that can be loaded on the column during the purification procedure. The primary economic factors important to the purification process (column throughput, solvent use, labor or time cycle) are directly related to the quantity of the mass loaded onto the column.

The dynamic capacity of the polymer resin is important since it is related to the mass transfer efficiency of the polymer for the particular molecule, and it dictates the time-scale under which the purification can occur. A low dynamic capacity indicates that the polymer matrix is not suitable for high-speed purification processes.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions:

| | | |
|---|---|---|
| MIBC | = | methyl isobutyl carbinol (4-methyl-2-pentanol) |
| DVB | = | divinylbenzene (mixture of meta/para isomers) |
| EVB | = | ethylvinylbenzene (mixture of meta/para isomers) |
| BPO | = | benzoyl peroxide |
| rpm | = | revolutions per minute |
| v/v | = | volume/volume |
| w/v | = | weight/volume |
| μm | = | micron |
| nm | = | nanometer |
| g/L | = | grams/Liter |
| cm³/g | = | cubic centimeter per gram |

-continued

| µl | = | microliter |
| NA | = | not analyzed |

EXAMPLE 1

This example illustrates the preparation of a macroporous polymer of the present invention.

An organic monomer phase was prepared in a 1-liter beaker by combining the following ingredients: 180 g divinylbenzene mixture (80% DVB/20% EVB), 73 g ortho-xylene, 147 g MIBC, and 10.6 g BPO (75% purity, 25% water). These amounts correspond to 122% mixed porogen (based on total monomer), a hydrophilic porogen/hydrophobic porogen ratio of 2.0, and 4.5% free radical initiator, BPO (based on total monomer). This mixture was stirred for 20 minutes under a nitrogen atmosphere.

To a 2-liter, 4-necked reaction flask equipped with a condenser, mechanical stirrer, thermocouple and nitrogen inlet, an aqueous solution was prepared by mixing together the following: 783 g deionized water, 5.0 g Culminal™ MHEC-8000 (methylhydroxyethyl cellulose, available from Hercules Chemical Company, viscosity of 8,000 milliPascal·second (mPa·s=centipoise, cP) for a 2% aqueous solution at 20° C.), 0.158 g sodium lauryl sulfate, 2.94 g 50% sodium hydroxide (aqueous) and 3.13 g boric acid. The solution was stirred at 250 rpm while the temperature was increased rapidly to 80° C., where it was held there for one hour. The solution was then cooled over a 30 minute period to ambient temperature by air cooling of the reaction vessel. After complete dissolution of the solid reactants, agitation was stopped and an organic phase (prepared above) was added to the reaction flask.

The reaction mixture (combined organic and aqueous phases) was stirred at 300 rpm at room temperature for 20 minutes and then heated to 80° C. over 47 minutes. The reaction mixture was held at 80° C. for 12 hours to polymerize the reactants. The reaction mixture was then transferred to a pressure vessel equipped for agitation, and heated at 100° C. for 5 hours to convert residual reactants and finish the polymerization.

After the polymerization reaction was complete, the temperature of the reaction mixture was adjusted to 50° C. while stirring. The pH of the aqueous phase of the aqueous/polymer mixture was adjusted to 5.0 by adding approximately 3 g boric acid followed by a slow addition of 10% sulfuric acid (aqueous) until the final pH was reached. A total of 25.0 grams of β-1,4-glucan-4-glucanhydrolase (Cellulase™ 4000, available from Valley Research, Inc.) was added to the aqueous/polymer mixture by sprinkling the enzyme powder into the reactor, in four equal weight charges, over 24 hours. The temperature was held at 50° C. throughout the enzyme treatment. The pH of the aqueous phase of the aqueous/polymer mixture was then adjusted to 12.0 with 50% sodium hydroxide (aqueous) and the temperature was raised to 90° C. where it was maintained for 2 hours. The aqueous/polymer mixture was cooled to room temperature, removed from the flask, and placed into a 1-liter chromatography column. The aqueous phase was filtered from the polymer, and then the packed bed of polymer was washed with 2 liters of deionized water, followed by 3.5 liters of acetone and finally with 7 liters of deionized water. The water wet polymer was then dried at a temperature of 100° C., under 2.5 mm (0.1 inch) mercury vacuum, for a period of 16 hours.

Polymers 1-4 through 1-11 were prepared according to the description provided above, except that the percent porogen, MIBC/xylene ratio and % BPO were varied as summarized in Table 1; polymer sample 1–6 corresponds to the description provided above. All polymers identified in Table 1 with the suffix "C" are considered to be comparative for the purposes of the present invention. Polymer samples 1–5 through 1–9 are considered representative of the macroporous polymers of the present invention. Polymer samples 1–12C, 1–13C and 1–14C are commercially available chromatographic-grade polyvinylaromatic polymers that were evaluated along with the polymer samples prepared according to the description above.

Commercial polymer 1–12C is a 30 µm particle size poly(styrene-divinyl-benzene) material available as Source™ 30RPC resin from Amersham-Pharmacia Company, Uppsala, Little Chalfont, UK. Commercial polymer 1–13C is a 15 µm particle size poly(styrene-divinylbenzene) material available as Source™ 15RPC from Amersham-Pharmacia Company, Uppsala, Little Chalfont, UK. Commercial polymer 1–14C is a 15 µm particle size poly(styrene-divinyl-benzene) material available as PLRP-S 300 resin from Polymer Labs Ltd., Shropshire, UK.

EXAMPLE 2

This example describes evaluation of the macroporous polymers of the present invention for insulin binding capacity. Samples of approximately 5 ml volume were packed into small-scale test columns (1.0 cm internal diameter×6.3 cm length) and evaluated for frontal adsorption of bovine insulin from aqueous solution; this test was designed to determine if the polymer matrix allowed rapid, efficient mass transfer and high capacity for a target probe molecule (for example, insulin) under typical use conditions. In addition, samples of approximately 20 ml were packed into larger-scale test columns (1.0 cm internal diameter×25 cm length) and a fractionation/separation of insulin was performed; this test was used to confirm that the polymer matrix provided satisfactory performance under typical process conditions.

Five grams of the dried polymer resin (prepared according to Example 1 unless indicated otherwise) was mixed with 35 ml of 20% ethanol/water (v/v), and allowed to stand at ambient temperature for at least 2 hours. The polymer slurry was then packed into an Omnifit™ glass column (dimensions: 6.3 cm length by 10 mm inner diameter, available from Millipore Corp.) by flow packing in 20% v/v ethanol/water solution at a linear velocity of 160 cm/hr. The quality of column packing was confirmed by injecting a 50 µL pulse of 1% sodium chloride solution in deionized water into the column, while flowing 20% v/v ethanol/water eluent at a linear velocity of 40 cm/hr. The efficiency (plates/meter) and asymmetry of the column were calculated using Hewlett Packard Chemstation™ Software. Target values for acceptable column packing parameters were a minimum of 5,000 plates/meter efficiency with asymmetry of 0.8 to 1.8.

A solution of bovine insulin (available from Sigma Chemical Co), at a concentration of 5 grams per liter of water, was prepared. A total of 200 ml of this solution was pumped into the column at a linear velocity of 150 cm/hr, and a UV spectrophotometric detector (Spectraflow™ 783, available from ABI Analytical, Kratos Division) set at a wavelength of 291 nm was used to monitor the bovine insulin in the effluent.

The dynamic capacity (g/L) of the polymer resin was obtained by recording the amount of insulin sorbed onto the polymer resin at the point of 10% insulin breakthrough (relative to the total amount of insulin sorbed onto the polymer resin) in the UV-response curve. The total capacity of the resin (g/L) was determined by measuring the insulin concentrations of the influent and effluent solutions by UV spectrophotometry, and then performing a mass balance. Results are summarized in the discussion under Example 3.

EXAMPLE 3

This example describes how the macroporous polymers of the present invention were evaluated for their permeability characteristics, that is, resistance to compression. The polymers are characterized by their "flow resistance" or 1/K values (see Equation 3).

In industrial high pressure liquid chromatography, it is common to use columns that are equipped with a piston that exerts a force (pressure) directly onto the resin. It is preferred to keep the piston actively compressing the bed at a pressure that is equal to or greater than the maximum anticipated flow pressure throughout the chromatographic cycle. In order to test the permeability characteristics of the polymers of the present invention, polymer resin was packed into a ProChrom™ Dynamic Axial Compression column (Model LC.50) and compressed with the piston set first at 10 and then at 60 bar compression pressure. The purpose of this testing was to characterize the permeability characteristics (resistance to compression) of each sample. A detailed description follows:

Approximately 100 g of dry polymer resin (corresponding to approximately 500 ml wet resin) was added to 700 ml of a solution of 20% ethanol/water (v/v) and allowed to stand at ambient temperature for at least 2 hours. This polymer sample was agitated into slurry form and poured into a 5 cm (internal diameter)×54 cm (length) ProChrom™ Dynamic Axial Compression L.C.50 316 L stainless steel column (manufactured by Prochrom S.A., France). A piston assembly (driven by external air pressure converted into hydraulic oil pressure) was activated to apply a variable pressure to the polymer resin bed. The piston was first set to deliver approximately 10 bar of hydraulic pressure; the resin bed was considered packed when the piston no longer moved. The height of the bed was then measured. A flow of 10 ml of a solution of 20% ethanol/water (v/v) was passed through the resin bed for 30 minutes to equilibrate the bed.

In general, to determine the interparticle void volume (or permeability) of the polyvinylaromatic polymer bed, the mobile phases must be selected for compatibility with the probe molecule such that they eliminate or reduce interaction of the probe molecule with the hydrophobic surface of the polyvinyl-aromatic polymer. Conventional probe molecules, such as linear polystyrene, Blue dextran and polyethylene glycol may be used, but require the use of non-polar mobile phases (such as tetrahydrofuran and toluene). The probe molecules used in the method described below, however, do not require the use of non-polar solvents and can be used in any aqueous-organic solvent system, for example, 20% ethanol.

To determine the total volume of voids in the column (both intraparticle and interparticle), 2 ml of 1% sodium chloride (w/v in 20% aqueous ethanol) was injected into the system. The salt was detected by a conductivity detector. To determine the interparticle voids volume only, a solution of 20% ethanol (aqueous) containing 1% (w/v) of a 0.1–0.9 μm ionically-charged emulsion polymer or finely ground ionically-charged polymer (for example, crosslinked polystyrene with ionizable functional groups, such as weak-acid functional group (carboxylate group), strong acid functional group (sulfonate), or quaternary ammonium chloride group) was injected into a stream of 20% ethanol (aqueous) flowing through the bed. The particles were detected by UV detector, got at 280 nm. Due to the size of the ionically-charged polymer probe particles, the particles did not penetrate the pores of the polymer resin of this invention. Due to the surface nature of the ionically-charged polymer probe particles (these particles had aromatic structure and a high concentration of ionogenic groups distributed throughout the surface) hydrophobic attraction/retention to the polymer resin of this invention was prevented.

Total void volume of the polymer bed (salt probe elution volume) was determined and combined with the void volume external to the polymer particles (ionically-charged emulsion or ground polymer elution volume). These values, together with the measured bed volume, were used to calculate $\epsilon$ in Equations 2 and 3. After testing at 10 bars, the same evaluation was conducted at 60 bars.

Table 1 summarizes the flow resistance and insulin capacity characteristics of the macroporous polymers of the present invention (Polymers 1–5 through 1–9) and various comparative polymers (Polymers with suffix C). See discussion under Example 1 for detailed description of the polymers and their corresponding identification in the Tables. Entries in Table 1 include percent porogen (based on total monomer), hydrophilic porogen/hydrophobic porogen ratio (MIBC/xylene) and % free radical initiator used (based on total monomer) to prepare the polymers; insulin capacities in g/L and flow resistance values at medium and high pressure; parenthetical ( ) entries after the individual values for insulin capacity and flow resistance for a given polymer sample indicate the number of different polymers prepared according to the same process (same percent porogen, hydrophilic porogen/hydrophobic porogen ratio and % BPO) that were tested and averaged together to generate the insulin capacity and flow resistance values shown in Table 1. Table 2 provides additional polymer properties (surface area, porosity) on selected samples.

Comparative polymer 1–1C illustrates that too high of a porogen level provides unsatisfactory compressibility at high pressure, whereas polymers 1–10C and 1–11C demonstrate that too low of a porogen level, while providing satisfactory compressibility (low flow resistance), produces extremely low insulin capacities. Comparative polymers 1–1C, 1–2C and 1–3C show that reducing the percent porogen level tends to improve the flow resistance properties; however, flow resistance performance remains unsatisfactory for high pressure operation, In addition, the dynamic insulin capacity becomes unsatisfactory with the combination of low percent porogen and low MIBC/xylene ratio (comparative polymer 1–4C).

Polymers 1–5 through 1–9 are representative of the unexpected combination of high insulin capacity and low flow resistance (at high pressure) performance provided by balancing the percent porogen and hydrophilic porogen/ hydrophobic porogen ratio parameters used to prepare the polymers of the present invention.

Commercial polymer samples 1–12C and 1–13C both exhibit unacceptable compressibility characteristics, although polymer 1–12C provides adequate insulin capacity performance. Although commercial polymer 1–14C provides marginally acceptable compressibility performance, insulin capacity is well below acceptable values.

TABLE 1

Flow Resistance and Insulin Capacity Properties

| Polymer | Percent Porogen | MIBC/Xylene | % BPO | Insulin Capacity: Dynamic/Total | 1/K at 10/60 Bar |
|---|---|---|---|---|---|
| 1-1 C | 178 | 1.2 | 1.5 | 86/92 | 1,870/17,300 |
| 1-2 C | 144 | 1.2 | 1.5 | 86/108 (3) | 1,870/10,100 (3) |
| 1-3 C | 144 | 1.2 | 4.5 | 86/121 | 1,050/7,300 |
| 1-4 C | 122 | 1.2 | 4.5 | 42/108 | NA |
| 1-5 | 122 | 1.6 | 4.5 | 71/113 | NA |
| 1-6 | 122 | 2.0 | 4.5 | 82/103 (4) | 890/4,060 (2) |
| 1-7 | 122 | 2.0 | 8.2 | 63/105 | 760/3,100 |
| 1-8 | 122 | 2.4 | 4.5 | 81/93 | NA |
| 1-9 | 122 | 2.7 | 4.5 | 79/91 | 1,050/3,500 |
| 1-10 C | 100 | 1.2 | 1.5 | 7/52 | NA |
| 1-11 C | 67 | 1.2 | 1.5 | 5/15 | 1,320/3,100 |
| 1-12 C | — | — | — | 86/91 | 1,180/12,000 |
| 1-13 C | — | — | — | NA | 1,600/8,570 |
| 1-14 C | — | — | — | 53/57 | 1,660/6,270 |

TABLE 2

Additional Polymer Properties

| Polymer ID | Surface Area (m$^2$/g) | Total Porosity (cm$^3$/g) | Operational Mesoporosity (cm$^3$/g) | Operational Microporosity (cm$^3$/g) | Macroporosity (cm$^3$/g) |
|---|---|---|---|---|---|
| 1-1 C | 743 | 2.3 | 0.76 | 0.3 | 1.2 |
| 1-3 C | 621 | 1.8 | 1.3 | 0.2 | 0.3 |
| 1-6 | 528 | 1.6 | 1.24 | 0.2 | 0.16 |
| 1-8 | 549 | 1.55 | 1.14 | 0.2 | 0.2 |
| 1-9 | 524 | 1.6 | 1.0 | 0.2 | 0.4 |
| 1-12 C | 611 | 2.8 | 0.8 | 0.2 | 1.8 |
| 1-13 C | 481 | 1.6 | 0.5 | 0.2 | 0.9 |
| 1-14 C | 299 | 1.3 | 0.7 | 0.1 | 0.5 |

EXAMPLE 4

This example describes the effect of preparing the macroporous polymers of the present invention with and without enzyme treatment. The enzyme treatment minimizes the clumping or agglomeration of polymer resins that sometimes occurs during use due to undesirable attractive forces between the beads arising from surface contamination (for example, ionic or charged materials) of the polymer. A particular advantage of using the enzyme treatment is that the resultant spherical polymer particles do not agglomerate, that is, particles do not adhere to one another to form clumps. The enzyme treatment is believed to clean and remove traces of dispersants and suspending aids (used during the polymerization process) from the surface of the polymer beads, thus providing polymer beads that flow freely and pack uniformly in columns, leading to minimum bed volumes and low pressure drop characteristics during use.

Five different samples of a macroporous polymer prepared similarly to that described in Example 1 were treated as follows: 4 portions (4A–4D) were treated with cellulase (described below) and one sample (4E) was not treated with cellulase; the samples were evaluated for their settling properties. Samples of each polymer resin (3.5 g dry, corresponding to about 25 ml wet dispersed volume) were weighed into 25-ml graduated cylinders. To each cylinder 20 mls of 20% ethanol (aqueous) was added. The cylinders were then stirred with a glass rod to provide a slurry and mixtures were allowed to settle for approximately 16 hours or overnight. The test samples were then restirred with a glass rod until fully mixed. After mixing the sample, the glass rod was removed and washed with of 20% ethanol (aqueous) and the total volume in the cylinders adjusted to 25.0 ml (approximately 0.5 ml of 20% ethanol was used to wash and adjust each sample). The samples were then observed for 4 days and the settled bed volumes (resin) were recorded as a function of time. The results are summarized in Table 3.

Enzyme Treatment of Polymer 4A (before high temperature cure): Approximately 250 ml of slurried resin (containing 150 ml of resin) was add to 2 liter, 4-necked flask equipped with a condenser, mechanical stirrer, thermocouple and nitrogen inlet. To the slurry, was added 100 ml of deionized water, the pH was adjusted to 5.0 using boric acid and 28 g of Cellulase™ 4000 (19% on polymer) was then added to the slurry. The mixture was heated to 37° C. and stirred for 3 hours. The reaction mixture was then transferred to a pressure vessel equipped for agitation, and heated at 100° C. for 5 hours. The aqueous/polymer mixture was cooled to room temperature, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was then dried at a temperature of 100° C., under 2.5 mm mercury vacuum, for a period of 16 hours.

Enzyme Treatment of Polymer 4B (after high temperature cure, before solvent wash): Approximately 250 ml of slurried resin (containing 150 ml of resin) was transferred to a pressure vessel equipped for agitation and heated at 100° C. for 5 hours. The aqueous/polymer mixture was cooled to room temperature and transferred to a 2-liter, 4-necked flask equipped with a condenser, mechanical stirrer, thermocouple and nitrogen inlet. To the slurry, was added 100 ml of deionized water, the pH was adjusted to 5.0 using boric acid and 28 g of Cellulase™ 4000 (19% on polymer) was then added to the slurry. The mixture was heated to 37° C. and stirred for 3 hours, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was then dried at a temperature of 100° C., under 2.5 mm mercury vacuum, for a period of 16 hours.

Enzyme Treatment of Polymer 4C (after high temperature cure, after solvent wash, before solvent re-wash): Approximately 250 ml slurred resin (containing 150 mls of resin) was transferred to a pressure vessel equipped for agitation and heated at 100° C. for 5 hours. The aqueous/polymer mixture was cooled to room temperature, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The mixture was transferred to a 2-liter, 4-necked flask equipped with a condenser, mechanical stirrer, thermocouple and nitrogen inlet. To the slurry, was added 100 ml of deionized water, the pH was adjusted to 5.0 using boric acid and 28 g of Cellulase™ 4000 (19% on polymer) was then added to the slurry. The mixture was heated to 37° C. and stirred for 3 hours, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was then dried at a temperature of 100° C., under 2.5 mm mercury vacuum, for a period of 16 hours.

Enzyme Treatment of Polymer 4D (after high temperature cure, after solvent wash, after drying polymer, before solvent re-wash): Approximately 250 ml of slurried resin (containing 150 ml of resin) was transferred to a pressure vessel equipped for agitation and heated at 100° C. for 5 hours. The aqueous/polymer mixture was cooled to room temperature, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was them dried at a temperature of 100° C., under 2.5 mm mercury vacuum, for a period of 16 hours. The dried sample was transferred to a 2-liter, 4-necked flask equipped with a condenser, mechanical stirrer, thermocouple and nitrogen inlet. To the slurry, was added 100 ml of deionized water, the pH was adjusted to 5.0 using boric acid and 28 g of Cellulase™ 4000 (19% on polymer) was then added to the slurry. The mixture was heated to 37° C. and stirred for 3 hours, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was then dried at a temperature of 100° C., under 2.5 mm mercury vacuum, for a period of 16 hours.

Treatment of Polymer 4E (without enzyme): Approximately 250 ml of slurried resin (containing 150 ml of resin) was transferred to a pressure vessel equipped for agitation and heated at 100° C. for 5 hours. The aqueous/polymer mixture was cooled to room temperature, removed from flask and placed into a 1-liter chromatography column. The aqueous phase was filtered from the polymer and the packed bed of polymer was washed with 7 liters of deionized water, followed by 3.5 liters of acetone and finally with 7 liters of deionized water. The water wet polymer was then dried at a temperature of 100° C., under 2.5 mm mercury vacuum, for a period of 16 hours.

The results in Table 3 demonstrate that the macroporous polymers of the present invention may be enzyme treated in a variety of ways to minimize clumping or agglomeration of the polymer particles. This is demonstrated by the compacted volume of the treated polymers (4A–4D) after only 18 hours of settling, representing 60% of the original dispersed volume of each sample, relative to the untreated polymer at 94% of its original dispersed volume.

TABLE 3

| Sample Settling Time, hrs | 4A Settled Volume (ml) | 4B Settled Volume (ml) | 4C Settled Volume (ml) | 4D Settled Volume (ml) | 4E Settled Volume (ml) |
|---|---|---|---|---|---|
| 0 | 25.0 | 25.0 | 25.0 | 25.0 | 25.0 |
| 1 | 23.8 | 23.8 | 22.0 | 23.5 | 24.0 |
| 2 | 23.0 | 22.9 | 20.0 | 22.0 | 24.0 |
| 3 | 21.8 | 21.6 | 19.5 | 21.3 | 24.0 |
| 4 | 20.5 | 20.8 | 18.8 | 19.2 | 24.0 |
| 5 | 19.8 | 20.2 | 18.1 | 18.9 | 24.0 |
| 6 | 19.0 | 19.7 | 17.5 | 18.5 | 24.0 |
| 7 | 18.5 | 19.2 | 17.0 | 18.0 | 24.0 |
| 8 | 18.1 | 18.4 | 16.5 | 17.5 | 24.0 |
| 18 | 15.0 | 15.0 | 15.1 | 15.1 | 23.5 |
| 24 | 14.9 | 14.9 | 15.0 | 15.0 | 23.5 |
| 48 | 14.9 | 14.9 | 15.0 | 15.0 | 23.5 |

Similarly, samples of enzyme-treated and non-enzyme-treated polymer resin were prepared and evaluated for pressure drop characteristics when used in column operations. Approximately 1200 ml of each resin slurry (containing about 550 ml of polymer resin) was placed into a 6.2 cm Amicon™ Vantage column. A 545 ml resin bed was formed and washed with 3 bed volumes of USP (United States Pharmacopoeia) grade water at 50 ml/min (178 cm/hr) using a Rainin™ HPLX pump, followed by a mixture of 65% acetone/35% USP grade water, and then finally washed with 99.5% acetone at 50 ml/min. The pressure was measured by using an Ashcroft™ pressure test gauge with a range of zero to $6.9 \times 10^6$ Pa (1000 psi or pounds per square inch) The samples treated with cellulase had reduced pressure drop across the column ($1.4 \times 10^5$ Pa or 20 psi) relative to the untreated sample ($1.4 \times 10^6$ Pa or 200 psi).

We claim:

1. A macroporous polymer comprising polymerized monomer units of:
   (a) 50 to 100 percent by weight of one or more polyvinylaromatic monomer, and
   (b) zero to 50 percent by weight of one or more monounsaturated vinylaromatic monomer;
   wherein the polymer has:
   (i) a total porosity of 0.7 to 2 cubic centimeter per gram;
   (ii) an operational mesoporosity of 0.7 to 1.9 cubic centimeter per gram;
   (iii) an average particle size diameter of 2 to 600 microns;
   (iv) a surface area of 200 to 1500 square meters per gram;
   (v) a flow resistance value from 700 to less than 1,800 at 10 bar pressure and from 1,500 to less than 7,000 at 60 bar pressure; and
   (vi) a total insulin capacity of 75 to 150 grams insulin/liter of polymer and a dynamic insulin capacity of 60 to 150 grams insulin/liter of polymer.

2. The polymer of claim 1 wherein the polyvinylaromatic monomer is selected from one or more of divinylbenzene, trivinylbenzene, divinyltoluene, divinylnaphthalene, divinylanthracene and divinylxylene.

3. The polymer of claim 1 wherein the monounsaturated vinylaromatic monomer is selected from one or more of styrene and ($C_1$–$C_4$)alkyl-substituted styrenes.

4. The polymer of claim 1 wherein the polymer has:
   (a) a surface area of 400 to 1000 square meters per gram;
   (b) an operational mesoporosity of 0.9 to 1.4 cubic centimeter per gram;
   (c) an average particle size diameter of 10 to 75 microns;
   (d) a flow resistance value from 700 to less than 1,500 at 10 bar pressure and from 1,500 to less than 5,000 at 60 bar pressure; and
   (e) a total insulin capacity of 90 to 150 grams insulin/liter of polymer and a dynamic insulin capacity of 75 to 150 grams insulin/liter of polymer.

5. The polymer of claim 1 comprising polymerized monomer units of:
   (a) 75 to 100 percent by weight of one or more polyvinylaromatic monomer, and
   (b) zero to 25 percent by weight of one or more monounsaturated vinylaromatic monomer.

6. The polymer of claim 1 wherein the polymer is selected from one or more of divinylbenzene copolymer, styrene-divinylbenzene copolymer, divinylbenzene-ethylvinylbenzene copolymer and styrene-ethylvinylbenzene-divinylbenzene copolymer.

7. The polymer of claim 1 wherein the polymer has an average particle size diameter of 2 to 150 microns.

8. The polymer of claim 1 wherein the polymer has an average particle size diameter from greater than 150 microns up to 600 microns.

9. A process for preparing the macroporous polymer of claim 1 comprising polymerizing zero to 50 percent monovinylaromatic monomer and 50 to 100 percent polyvinylaromatic monomer, in the presence of 100 to 170 percent of a porogen mixture comprising a hydrophobic porogen and a hydrophilic porogen, and 0.5 to 10 percent free radical polymerization initiator, in an aqueous suspension; wherein all percent amounts are based on total weight monomer; and wherein:

(a) the hydrophilic porogen is present in a weight ratio of greater than 1.2/1 up to 3/1 relative to the hydrophobic porogen; and (b) the hydrophilic porogen is selected from one or more ($C_4$–$C_{10}$)alkanol and the hydrophobic porogen is selected from one or more ($C_7$–$C_{10}$)aromatic hydrocarbon and ($C_6$–$C_{12}$)saturated hydrocarbon.

10. The process of claim 9 wherein the hydrophilic porogen is selected from one or more ($C_5$–$C_8$)alkanol and the hydrophobic porogen is selected from one or more ($C_7$–$C_{10}$)aromatic hydrocarbon.

11. The process of claim 10 wherein the ($C_5$–$C_8$)alkanol is methyl isobutyl carbinol and the ($C_7$–$C_{10}$)aromatic hydrocarbon is xylene.

12. The process of claim 9 further comprising treating the macroporous polymer with an enzyme selected from one or more of cellulose-decomposing enzyme and proteolytic enzyme, wherein the enzyme is contacted with the macroporous polymor during polymerization, following polymerization, or after isolation of the polymer.

13. The process of claim 12, wherein the cellulose-decomposing enzyme is selected from one or more of β-1,4-glucan-4-glucanohydrolase, β-1,4-glucan-4-glucanohydrase, β-1,4-glucan-4-glucohydrase and β-1,4-glucan-4-cellobiohydrase.

14. The process of claim 9 wherein the porogen mixture is present at 115 to 150 percent, based on total weight of monomer.

15. The process of claim 9 wherein the hydrophilic porogen is present in a weight ratio from 1.4/1 to 2.5/1 relative to the hydrophobic porogen.

16. The process of claim 9 wherein the free radical initiator is present at 2 to 7 percent, based on total weight of monomer, and is selected from one or more diacyl peroxide and peroxyester.

17. The process of claim 16 wherein the diacyl peroxide is benzoyl peroxide.

18. A method for purifying aqueous solutions of mixed biomolecules, comprising contacting the aqueous solution with the macroporous polymer of claim 1 in a liquid chromatography column having an internal diameter of 2 to 100 centimeters, wherein the column is operated at a pressure of 10 to 100 bar.

19. The method of claim 18 wherein the column has an internal diameter of 10 to 50 centimeters and is operated at a pressure of 20 to 80 bar.

* * * * *